United States Patent [19]
DeBruin et al.

[11] Patent Number: 5,432,203
[45] Date of Patent: Jul. 11, 1995

[54] PROCESS OF RECOVERING COMPONENTS FROM POLYESTER RESINS

[75] Inventors: Bruce R. DeBruin, Kingsport, Tenn.; Andrius A. Naujokas, Webster; William J. Gamble, Rochester, both of N.Y.

[73] Assignee: Eastman Kodak Company, Rochester, N.Y.

[21] Appl. No.: 353,863

[22] Filed: Dec. 12, 1994

[51] Int. Cl.$^6$ .............................................. C08J 11/04
[52] U.S. Cl. ................................. 521/48.5; 521/48; 528/481; 528/496
[58] Field of Search ................ 521/48, 48.5; 528/496, 528/481

[56] References Cited

U.S. PATENT DOCUMENTS

| | | | |
|---|---|---|---|
| 5,051,528 | 9/1991 | Naujokas et al. | 560/78 |
| 5,298,530 | 3/1994 | Gamble et al. | 521/48.5 |

*Primary Examiner*—Morton Foelak
*Attorney, Agent, or Firm*—Joshua G. Levitt

[57] ABSTRACT

There is described a process and optimal conditions for depolymerizing polyester into its components and separating the components using apparatus comprising:
- a dissolver for receiving polyester,
- a reactor for depolymerizing polyester into components, and
- a rectifier for separating polyester components; the process comprising the steps of:
  a) adding polyester to the dissolver and combining it with melt from the reactor and liquid from the rectifier to reduce the chain length of the polyester,
  b) transferring reduced chain length polyester from the dissolver to the reactor,
  c) passing super-heated methanol through the reactor to depolymerize polyester into its constituent monomers;
  d) transferring depolymerization products from the reactor to the rectifier; and
  e) separating the depolymerization products in the rectifier into a vapor phase containing component monomers and a liquid phase containing higher molecular weight materials.

10 Claims, 1 Drawing Sheet

PROCESS OF RECOVERING COMPONENTS FROM POLYESTER RESINS

FIELD OF INVENTION

This invention relates to a process for recovery of monomer components from condensation-type polyester resins such as polyethylene terephthalate and polyethylene naphthalate.

BACKGROUND OF THE INVENTION

Polyester resins have found widespread use in varied applications. Polyester resins, such as polyethylene terephthalate and polyethylene naphthalate, are used in films, including photographic film and magnetic tape, in fibers, and in food containers such as bottles and beverage containers. Various methods have been disclosed for the depolymerization of such resins into their component monomers, such as ethylene glycol, terephthalic acid, naphthalic acid, or derivatives thereof, so that they could be reused.

U.S. Pat. No. 5,051,528 describes a process of recovering ethylene glycol and dimethyl terephthalate from polyethylene terephthalate scrap resins by dissolving the polyester resin in oligomers of the same monomers as present in the polyester, passing superheated methanol through the solution and recovering ethylene glycol and dimethyl terephthalate.

Commonly assigned, copending U.S. patent application Ser. No. 07/981,688 describes an improvement in the process of the '528 patent in which the scrap resin is combined with reactor melt in a dissolver, before the dissolver melt is transferred to a reactor for contact with super-heated methanol. In one embodiment, the polyester is combined in the dissolver with, in addition to reactor melt, other components exiting the reactor.

Other art describing recovery of monomer from polyester resins is noted in the above patent and application.

SUMMARY OF THE INVENTION

The present invention improves upon the process of the '528 patent and the '688 application by providing optimal ways of controlling the viscosity of the melt in the dissolver and results in optimal residence times and heat transfer characteristics. This permits efficient recovery of monomer from polyester resin.

Thus, in one embodiment the present invention provides a process for depolymerizing polyester into its components and separating the components using apparatus comprising:

a dissolver for receiving polyester, a reactor for depolymerizing polyester into components, and a rectifier for separating polyester components; the process comprising the steps of:

a) adding polyester to the dissolver and combining it with melt from the reactor and liquid from the rectifier to reduce the chain length of the polyester, b) transferring reduced chain length polyester from the dissolver to the reactor, c) passing super-heated methanol through the reactor to depolymerize polyester into its constituent monomers;

d) transferring depolymerization products from the reactor to the rectifier; and e) separating the depolymerization products in the rectifier into a vapor phase containing component monomers and a liquid phase containing higher molecular weight materials;

wherein i) the dissolver is operated at a temperature of 180° to 270° C. and a pressure of 80 to 150 kilopascals absolute (kPaa), ii) the reactor is operated at a temperature in the range of 180° to 305° C., and a pressure in the range of 101 to 800 kPaa, iii) the relative proportions, on a weight basis, of melt from the reactor and liquid from the rectifier fed to the dissolver is in the range of 0 to 1 parts liquid per part melt, and iv) the relative proportions on a weight basis of reactor melt plus rectifier liquid and polyester fed to the dissolver is in the range of 0 to 10 parts reactor melt plus rectifier liquid per part polyester, so that the viscosity of the polyester exiting the dissolver is maintained in the range of 0.001 to 0.2 Pascal seconds (Pa·s).

In a preferred embodiment, the dissolver is operated at a temperature in the range of 215° to 260° C. and a pressure in the range of 90 to 130 kPaa, the reactor is operated at a temperature in the range of 220° to 285° C., and a pressure in the range of 200 to 620 kPaa, the relative proportions, on a weight basis, of melt from the reactor and liquid from the rectifier fed to the dissolver is in the range of 0 to 0.5 parts liquid per part melt, the relative proportions on a weight basis of reactor melt plus rectifier liquid and polyester fed to the dissolver is in the range of 0.2 to 1 parts reactor melt plus rectifier liquid per part polyester, and the viscosity of the polyester exiting the dissolver is maintained in the range of 0.002 to 0.1 Pa·s In a particularly preferred embodiment, the dissolver is operated at a temperature in the range of 240° to 255° C. and a pressure in the range of 95 to 105 kPaa, the reactor is operated at a temperature in the range of 250° to 280° C., and a pressure in the range of 240 to 410 kPaa, the relative proportions, on a weight basis, of melt from the reactor and liquid from the rectifier fed to the dissolver is in the range of 0 to 0.25 parts liquid per part melt, the relative proportions on a weight basis of reactor melt plus rectifier liquid and polyester fed to the dissolver is in the range of 0.2 to 0.4 parts reactor melt plus rectifier liquid per part polyester, and the viscosity of the polyester exiting the dissolver is maintained in the range of 0.01 to 0.04 Pa·s.

When operated in this way, the residence time of the polyester in the dissolver required to completely liquify the polyester is in the range of 10 to 90 minutes. Preferably it is in the range of 10 to 70 minutes and most preferably it is in the range of 30 to 65 minutes. Average residence time in the dissolver is equal to the volume of material in the dissolver divided by the rate at which material exits the dissolver.

We have found that for optimal recovery of materials, a scrubber should be connected to the dissolver to remove terephthalate contained in the gas that exits the dissolver. This use of the scrubber leads results in an advantage accruing from using both rectifier liquid and reactor melt to control the viscosity of the dissolver melt. Rectifier liquid is more effective than reactor melt for producing the desired viscosity and other desired parameters like residence time and heat transfer characteristics. However, rectifier liquid also produces more gases that need to be sent to the scrubber. By controlling the ratio of rectifier liquid to reactor melt, one obtains the optimum benefits for the dissolver, while minimizing the impact on the scrubber. One must maintain a balance between the condition where not enough rectifier liquid is used that the viscosity can not be maintained at the desired level and the condition where so much rectifier liquid is used that the scrubber is overloaded with gas. While in the ideal system, no rectifier liquid would be used, in a practical system, some rectifier liquid is needed to maintain the viscosity and the desired level. This typically is achieved when the ratio of rectifier liquid to reactor melt is in the range of 0.01 to 0.5 parts by weight, and more frequently in the range of 0.05 to 0.25 parts by weight.

In the following description of this invention polyethylene terephthalate will be used to illustrate the practice of the invention. It will be understood that the invention also is applicable to other condensation polyesters, such as polyethylene naphthalate.

DESCRIPTION OF THE PREFERRED EMBODIMENTS

Figure 1:
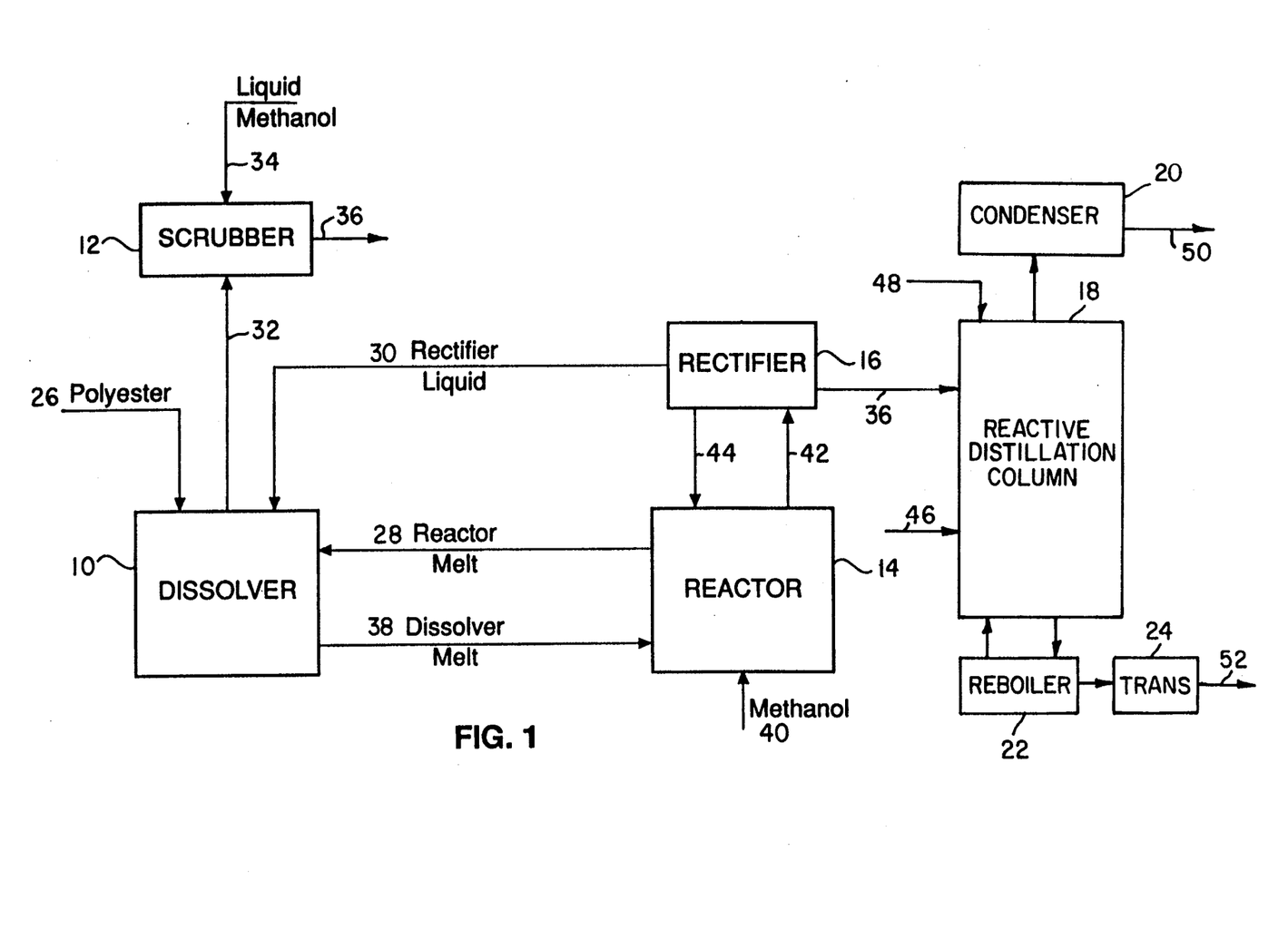
FIG. 1 is a schematic flow diagram illustrating the process of this invention.

FIG. 1 schematically illustrates apparatus to carry out the process of the invention. It comprises a dissolver 10, a reactor 12 and a rectifier 14, connected by the pipes, pumps and valves to transfer the materials in accordance with the process of the invention. Also shown is a scrubber 16, for recovering gases from the dissolver, and a recovery device 18, for recovering monomer components and methanol vapor exiting the rectifier.

In practice polyethylene terephthalate (20) in a suitable form and size is introduced into the dissolver by any suitable means where it is liquified and reduced in chain length. The dissolver can be run at atmospheric pressure. Thus, simple solids handling devices such as rotary air locks can be employed to introduce the polyester resin. Suitable means for introducing the polyester include an air conveyor, a screw feeder, an extruder, and the like.

The dissolver is equipped with means for heating its contents to a temperature of up to about 305° C. In practice the dissolver is maintained at a temperature in the range of 240° to 260° C.

Reactor melt (22) and rectifier liquid (24) are introduced into the dissolver via suitable piping. Valves can be placed in their flow path to control the rate of introduction of these materials and their relative proportions. The reactor and rectifier are run at a higher pressure than the dissolver, thus eliminating the need for pumping means to transfer reactor melt and rectifier liquid to the dissolver, although pumping means can be employed, if desired.

Reactor melt and rectifier liquid introduced into the dissolver react with the polyester to shorten the average chain length. This initiates the depolymerization reaction and decreases the viscosity of the dissolver contents. In addition, there can be added to the dissolver an ester exchange catalyst, such as zinc acetate. Such catalysts are known in the art to facilitate the depolymerization process. The catalyst can be employed in a range of 0 to 800 parts by weight per million parts by weight of solid polyester introduced into the dissolver (ppm polyester). Preferably the catalyst is employed in the range of 30 to 300 ppm polyester, and most preferably the catalyst is employed in the range of 30 to 100 ppm polyester.

In a preferred embodiment, the melt in the dissolver is protected from the atmosphere by a blanket of nitrogen. This reduces degradation of the dissolver melt due to oxidation reactions.

The reactor melt and dissolver melt comprise methanol, low molecular weight polyesters, monomers, monohydric alcohol-ended oligomers, glycols, and dimethylterephthalate and methylhydroxyethyl terephthalate.

The major difference between these two melts is the average chain length of the polyester. The rectifier liquid contains the same components except for polyesters.

As indicated above, the viscosity of the dissolver melt is maintained in the range of 0.002 to 0.1 Pa·s. This is sufficiently low to permit the use of inexpensive pumping and heating means, and permits the reactor to be operated at optimum pressures to provide good yields of monomer. The flow rates of material in and out of the dissolver can be adjusted to maintain the viscosity at the desired level.

The dissolver also can be equipped with means for removing contaminants that are introduced with the polyester. Most contaminants are removed from the melt in the dissolver before introduction of the dissolver melt to reactor. Inorganic contaminants such as metals or sand are removed by a filter. Polyolefins and other contaminants that float on top of the dissolver melt are drawn off.

The gases (26) which evolve in the dissolver contain monomers that preferably are recovered together with the monomers exiting the reactor. This can be accomplished by passing the gases to the scrubber where they are treated with and absorbed by liquid methanol (28). This material (30) is then passed to the recovery device where it is combined with material (32) exiting the rectifier for recovery of the monomers.

Melt (34) from the dissolver is transferred to the reactor by suitable piping and pumps. If desired, a portion of the melt can be recirculated to the top of the dissolver to aid in the submersion of solid polyester being introduced into the dissolver. Alternatively or additionally, the reactor melt can be introduced into the dissolver to aid in the submersion of solid polyester.

Super-heated methanol vapor (36) can be provided to the reactor by conventional means. A preferred means is described in U.S. Pat. No. 5,051,528 to supply the methanol to the reactor and recover the methanol for reuse. The methanol introduced into the reactor heats the reactor contents and acts as a depolymerization agent. The effectiveness of the super-heated methanol for heating the reactor contents and for stripping gases depends on its volumetric flow rate; the depolymerization rate in the reactor therefore is a function of the methanol flow rate to the reactor. Methanol is introduced into the reactor at a rate in the range of 2 to 6 parts by weight methanol per part polyester.

There is transferred from the reactor to the rectifier a vapor stream (38) comprising methanol, dimethylterephthalate, glycols including ethylene glycol, diethylene glycol, and triethylene glycol, dimethylisophthalate, cyclohexanedimethanol, and methylhydroxyethyl terephthalate. The rectifier separates methylhydroxyethyl terephthalate from the vapor stream exiting the reactor and returns it to the dissolver in the form of a liquid (40) together with dimethyl terephthalate, glycols and methanol. Excess liquid (42) from the rectifier drains back into the reactor.

The remainder of the vapor stream (44) is transferred from the rectifier to recovery apparatus, where methanol (46) can be recovered for further use, and the glycol components (48) separated from the terephthalate components (50).

The invention has been described by reference to preferred embodiments, but it will be understood changes can be made to the apparatus and process steps specifically described herein within the spirit and scope of the invention.

What is claimed is:

1. A process for depolymerizing polyester into its components and separating the components using apparatus comprising:
    a dissolver for receiving polyester,
    a reactor for depolymerizing polyester into components, and
    a rectifier for separating polyester components; the process comprising the steps of:
    a) adding polyester to the dissolver and combining it with melt from the reactor and liquid from the rectifier to reduce the chain length of the polyester,
    b) transferring reduced chain length polyester from the dissolver to the reactor,
    c) passing super-heated methanol through the reactor to depolymerize polyester into its constituent monomers;
    d) transferring depolymerization products from the reactor to the rectifier; and
    e) separating the depolymerization products in the rectifier into a vapor phase containing component monomers and a liquid phase containing higher molecular weight materials;
    wherein
    i) the dissolver is operated at a temperature of 180° to 270° C. and a pressure of 80 to 150 kPaa,
    ii) the reactor is operated at a temperature in the range of 180° to 305° C., and a pressure in the range of 101 to 800 kPaa,
    iii) the relative proportions, on a weight basis, of melt from the reactor and liquid from the rectifier fed to the dissolver is in the range of 0 to 1 parts rectifier liquid per part reactor melt, and
    iv) the relative proportions, on a weight basis, of reactor melt plus rectifier liquid and polyester fed to the dissolver is in the range of 0 to 10 parts reactor melt plus rectifier liquid per part polyester, so that the viscosity of the polyester exiting the dissolver is maintained in the range of 0.001 to 0.2 Pa·s.

2. A process of claim 1, wherein the polyester resin is polyethylene terephthalate.

3. A process of claim 1, wherein the melt transferred from the reactor to the dissolver is comprised of depolymerization products and methanol.

4. A process of claim 1, where in the liquid transferred from the rectifier to the dissolver is comprised of methylhydroxyethyl terephthalate, dimethylterephthalate and methanol.

5. A process of claim 1, wherein:
    the dissolver is operated at a temperature in the range of 215° to 260° C. and a pressure in the range of 90 to 130 kPaa,
    the reactor is operated at a temperature in the range of 220° to 285° C., and a pressure in the range of 200 to 620 kPaa,
    the relative proportions, on a weight basis, of melt from the reactor and liquid from the rectifier fed to the dissolver is in the range of 0 to 0.5 parts liquid per part melt,
    the relative proportions on a weight basis of reactor melt plus rectifier liquid and polyester fed to the dissolver is in the range of 0.2 to 1 parts reactor melt plus rectifier liquid per part polyester, and the viscosity of the polyester exiting the dissolver is maintained in the range of 0.002 to 0.1 Pa·s.

6. A process of claim 1, wherein:
    the dissolver is operated at a temperature in the range of 240° to 255° C. and a pressure in the range of 95 to 105 kPaa,
    the reactor is operated at a temperature in the range of 250° to 280° C., and a pressure in the range of 240 to 410 kPaa,
    the relative proportions, on a weight basis, of melt from the reactor and liquid from the rectifier fed to the dissolver is in the range of 0 to 0.25 parts liquid per part melt,
    the relative proportions on a weight basis of reactor melt plus rectifier liquid and polyester fed to the dissolver is in the range of 0.2 to 0.4 parts reactor melt plus rectifier liquid per part polyester, and the viscosity of the polyester exiting the dissolver is maintained in the range of 0.01 to 0.04 Pa·s.

7. A process of claim 1, wherein the apparatus further comprises a scrubber for recovering gases exiting the dissolver.

8. A process of claim 1, wherein there is added to the dissolver an ester exchange catalyst in the amount of 1 to 800 ppm polyester.

9. A process of claim 1 wherein the average residence time of the polyester is in the range of 10 to 90 minutes.

10. A process of claim 5 wherein the ratio of rectifier liquid to reactor melt is in the range of 0.01 to 0.5 parts by weight.

* * * * *

UNITED STATES PATENT AND TRADEMARK OFFICE
CERTIFICATE OF CORRECTION

PATENT NO. : 5,432,203

DATED : July 11, 1995

INVENTOR(S) : DeBruin et al.

It is certified that error appears in the above-indentified patent and that said Letters Patent is hereby corrected as shown below:

Title page and columns 1-6 should be deleted and substitute the attached.

Signed and Sealed this

Thirtieth Day of January, 1996

Attest:

BRUCE LEHMAN

Attesting Officer

Commissioner of Patents and Trademarks

United States Patent [19]

DeBruin et al.

[11] Patent Number: 5,432,203
[45] Date of Patent: Jul. 11, 1995

[54] PROCESS OF RECOVERING COMPONENTS FROM POLYESTER RESINS

[75] Inventors: Bruce R. DeBruin, Kingsport, Tenn.; Andrius A. Naujokas, Webster; William J. Gamble, Rochester, both of N.Y.

[73] Assignee: Eastman Kodak Company, Rochester, N.Y.

[21] Appl. No.: 353,863

[22] Filed: Dec. 12, 1994

[51] Int. Cl.⁶ ............................................. C08J 11/04
[52] U.S. Cl. ................................... 521/48.5; 521/48; 528/481; 528/496
[58] Field of Search .................. 521/48, 48.5; 528/496, 528/481

[56] References Cited

U.S. PATENT DOCUMENTS

| | | | |
|---|---|---|---|
| 5,051,528 | 9/1991 | Naujokas et al. | 560/78 |
| 5,298,530 | 3/1994 | Gamble et al. | 521/48.5 |

*Primary Examiner*—Morton Foelak
*Attorney, Agent, or Firm*—Joshua G. Levitt

[57] ABSTRACT

There is described a process for the depolymerization of polyethylene terephthalate to monomer that can be used as a starting material for preparation of polyethylene terephthalate. The process described in U.S. Pat. No. 5,298,530, is extended to convert the ethylene glycol and dimethyl terephthalate resulting from that process to bis(hydroxyethyl) terephthalate which can be used directly as feedstock for the formation of polyethylene terephthalate.

10 Claims, 1 Drawing Sheet

PROCESS OF RECOVERING COMPONENTS FROM POLYESTER RESINS

FIELD OF INVENTION

This invention relates to a process for recovering ester and glycol components from condensation-type polyester resins and then converting them to monomer that can be used directly to prepare polyester resin.

BACKGROUND OF THE INVENTION

Polyester resins have found widespread use in varied applications. Polyesters such as polyethylene terephthalate are used in photographic film, in magnetic tape, in fibers, and in food and beverage containers. Various methods have been disclosed for the depolymerization of such resins into their component monomers, such as ethylene glycol and terephthalic acid or derivatives thereof, so that they can be reused.

Naujokas et al. U.S. Pat. No. 5,051,528 describes a process of recovering ethylene glycol and dimethyl terephthalate from polyethylene terephthalate scrap resins by dissolving the polyester resin in oligomers of the same monomers as are present in the polyester, passing super-heated methanol through the solution and recovering ethylene glycol and dimethyl terephthalate.

Gamble et al. U.S. Pat. No. 5,298,530, issued Mar. 29, 1994 improves on the process of the '528 patent by combining scrap resin with reactor melt in a dissolver before the dissolver melt is transferred to the reactor for contact with super-heated methanol. In the reactor, polymers and oligomers are further depolymerized into the component glycol and ester monomers, which are then recovered.

Toot et al. U.S. Pat. application Ser. No. 08/209,150, filed Mar. 10, 1994 optimizes the processes of Naujokas et al. and Gamble et al., cited above.

The processes described in these patents have numerous advantages. These include low cost, high efficiency, the ability to operate at relatively low pressure and the ability to be used with a variety of forms of polyester of varying degrees of cleanliness and purity.

The output of these processes is ethylene glycol and dimethylterephthalate. Typically, these monomers are separated and purified before being used further. It would be desirable if the output of these processes could be converted directly to starting material for polymerization of polyester. However prior attempts by the present inventors to accomplish this have resulted in starting material which is of insufficient purity to be useful. This is believed to be due to need to handle the monomers under conditions that would cause breakdown of the components into colored products. We have found that by configuring the apparatus and performing the processes under conditions that avoid localized heating and the presence of oxidants, monomer of acceptable purity can be obtained.

SUMMARY OF THE INVENTION

Our invention is a process for depolymerization of polyethylene terephthalate to monomer that can be used as a starting material for preparation of polyethylene terephthalate. The process is simple, uses uncomplicated equipment and avoids the need for multiple recovery operations. Preferably the process is continuous in nature, with the output of one step being transferred directly to the next step without any intermediate recovery or handling.

Specifically, the process described in U.S. Pat. No. 5,298,530, is extended to convert ethylene glycol and dimethyl terephthalate to bis(hydroxyethyl)terephthalate, which then can be used as feedstock for the formation of polyethylene terephthalate.

Thus, the present invention provides a process for converting scrap polyester directly to monomer that can be used to reform the polyester without the need to separate and purify the monomer components. The apparatus used to carry out the process of the present invention is similar to that used for the process described in U.S. Pat. No. 5,298,530, except that it adds a reactive distillation column and a reboiler. Optionally it can be used with one or more additional transesterification reactor stages as well as prepolymerization and polymerization stages.

The apparatus for carrying out the present invention comprises:
- a dissolver for receiving polyester,
- a reactor for depolymerizing polyester into monomer components,
- a rectifier for separating monomer components from high boiling impurities;
- a reactive distillation column for separating monomer components from low boiling impurities, for initiating an ester exchange reaction between dimethyl terephthalate and ethylene glycol to form bis(hydroxyethyl)terephthalate and for converting dimethyl terephthalate and ethylene glycol to bis(hydroxyethyl)terephthalate; and
- a reboiler from which heated ethylene glycol is introduced to the distillation column and where the ester exchange reaction is continued or completed.

The process comprises the steps of:
a) adding polyester to the dissolver and combining it with melt from the reactor to reduce the chain length of the polyester,
b) transferring reduced chain length polyester from the dissolver to the reactor,
c) passing super-heated methanol through the reactor to depolymerize polyester,
d) transferring depolymerization products from the reactor to the rectifier;
e) separating the depolymerization products in the rectifier into a vapor phase, containing methanol and monomer components, and a liquid phase, containing higher molecular weight materials;
f) transferring the vapor phase to a distillation column;
g) introducing ethylene glycol and an esterification catalyst into the distillation column
  i) to initiate a transesterification reaction between dimethyl terephthalate and ethylene glycol, and
  ii) to remove lower boiling components; and
h) continuing the transesterification reaction to form bis(hydroxyethyl) terephthalate.

a reboiler, or optionally in one or more additional reactors.

The transesterification reaction in step (h) can be continued in any combination of the reactive distillation column, the reboiler and additional transesterification reactors. The bis(hydroxyethyl)terephthalate resulting from this step can be recovered or passed directly to polymerization reactors to form polyethlyene terephthalate.

Steps a) through e) of the above process, and the equipment used to perform them, are summarized below and are described in detail in the above referenced Gamble et al. U.S. Pat. No. 5,298,530 and in copending, commonly assigned Toot et al. U.S. Pat. application Ser. No. 209,150 filed Mar. 10, 1994, the disclosures of which are incorporated herein by reference. The remainder of the process, and the equipment used to perform it, is described in detail below.

DETAILED DESCRIPTION OF THE INVENTION

FIG. 1 schematically illustrates apparatus to carry out the process of the invention.

The apparatus depicted in FIG. 1 comprises a dissolver (10), a scrubber (12) a reactor (14), a rectifier (16), a reactive distillation column (18), a condenser (20) a reboiler (22), and one or more optional transesterification reactors (24) connected by the pipes, pumps and valves to transfer the materials in accordance with the process of the invention.

Polyethylene terephthalate (26) in a suitable form and size is introduced into the dissolver by any suitable means where it is liquefied and reduced in chain length. The dissolver can be run at atmospheric pressure, or slightly positive or negative pressure, and is equipped with means for heating its contents to a temperature of up to about 305° C. The dissolver is maintained at a temperature in the range of 240° to 260° C.

Reactor melt (28), and optionally rectifier liquid (30), are introduced into the dissolver via means that can be used to control the rate of introduction of these materials and their relative proportions. The reactor and rectifier can be run at a higher pressure than the dissolver.

Reactor melt, and optional rectifier liquid, introduced into the dissolver react with the polyester to shorten the average chain length. This initiates the depolymerization reaction and decreases the viscosity of the dissolver contents. There can be added to the dissolver an ester exchange catalyst, such as zinc acetate. Preferably the catalyst is employed in the range of 30 to 300 ppm polyester, and most preferably the catalyst is employed in the range of 30 to 100 ppm polyester.

In a preferred embodiment there is added to the dissolver sufficient base to neutralize any acid formed from contaminants that may be carried into the dissolver with the polyester scrap. Suitable bases are sodium hydroxide, potassium hydroxide, lithium hydroxide, aluminum hydroxide, sodium carbonate, potassium carbonate, and the like. If used, sufficient base is added to maintain the pH equivalent of the melt in the range of 7 to 10; preferably 7 to 8.

In a preferred embodiment, the melt in the dissolver is protected from the atmosphere by a blanket of inert gas, such as nitrogen, carbon dioxide, argon, etc. This reduces degradation of the dissolver melt due to oxidation reactions.

The reactor and dissolver melts comprise methanol, low molecular weight polyesters, monomers, monohydric alcohol-ended oligomers, glycols, and dimethyl terephthalate and methylhydroxyethyl merephthalate. The major difference between these two melts is the average chain length of the polyester. The rectifier liquid contains the same components except for polyesters.

The viscosity of the dissolver melt preferably is maintained in the range of 0.002 to 0.1 Pa·s. This is sufficiently low to permit the use of inexpensive pumping and heating means, and permits the reactor to be operated at optimum pressures to provide good yields of monomer. The flow rates of material in and out of the dissolver can be adjusted to maintain the viscosity at the desired level.

The low boiling components (32) which evolve in the dissolver contain monomers that preferably are recovered together with the monomers exiting the reactor. This can be accomplished by passing them to the scrubber where they are treated with and absorbed by liquid methanol (34). This material (36) can be combined with material (50) exiting the condenser, with which it can be recovered in a separate process. Melt (38) from the dissolver is transferred to the reactor.

Super-heated methanol vapor (40) can be provided to the reactor by conventional means. The methanol introduced into the reactor heats the reactor contents and acts as a depolymerization agent. Methanol is introduced into the reactor at a rate in the range of 2 to 6 parts by weight methanol per part polyester. The reactor can be operated at a temperature in the range of 240° to 300° C. and at atmospheric to slightly elevated pressure, up to about 800 kPa.

There is transferred from the reactor to the rectifier a vapor stream (42) comprising methanol, dimethylterephthalate, glycols including ethylene glycol, diethylene glycol, and triethylene glycol, dimethylisophthalate, cyclohexanedimethanol, and methylhydroxyethyl terephthalate. The rectifier separates higher boiling components, such as methylhydroxyethyl terephthalate, from the vapor stream exiting the reactor and returns it to the reactor (44) in the form of a liquid. Part or all of this liquid (30) can be sent to the dissolver to adjust viscosity. The vapor stream (36) exiting the rectifier is transferred to a reactive distillation column.

The reactive distillation column is conventional and comprises a column filled with packing media that will provide a surface area sufficient for the transesterification reaction to take place. Typically it will comprise sufficient ideal stages to permit the reaction to occur. The reactive distillation column typically will have from 2 to 10 ideal stages and preferably will have 4 to 6 ideal stages. Depending upon the size of the reactive distillation column, the transesterification reaction can be completed in it, in the reboiler or in one or more optional additional transesterification reactors (24) beyond the reboiler. Typical residence times in the reactive distillation column are from 20 to 120 minutes, preferably from 20 to 60 minutes.

The vapor stream from the rectifier preferably is introduced toward the midpoint of the reactive distillation column, although it can be introduced at other convenient locations, such as at or near the bottom of the distillation column. Sufficient additional ethylene glycol (46) is introduced into the column to convert all of the dimethylterephthalate to bis(hydroxyethyl) terephthalate. The additional ethylene glycol can be introduced into the column as a vapor or a liquid. Typically, when introduced as a vapor, it is introduced at the bottom of the column. When introduced as a liquid, it typically is introduced at the top of the column. Generally, a transesterification catalyst (48), such as zinc acetate, is introduced at the top of the column and one or more known polymerization stabilizers can be introduced toward the bottom of the column. There can also be added to this column comonomers that ultimately will be incorporated into the polyester to modify its properties. However, it is preferred that such comonomers be added subsequently to improve control over their addition. The column preferably is operated at a temperature in the range of 100° to 200° C. and at atmospheric pressure, although it could be operated at elevated or reduced pressure and correspondingly modified temperature.

On the top of the reactive distillation column is a condenser from which excess and reaction methanol (50) is removed. As described in the example which follows, the condenser temperature and pressure can be used to regulate the ethylene glycol balance in the column.

A residence time in the reactive distillation column typically of about an hour is required to complete the transesterification reaction. If the distillation column is of such a size that residence time in it is not sufficient to cause full transesterification the reaction can be completed in the reboiler or in one or more reactors downstream of the reboiler. The reboiler is maintained at a temperature in the range of 190° to 210° C. at atmospheric pressure. It provides a source of ethylene glycol to the reactive distillation column. If sufficient ethylene glycol to drive the transesterification reaction is not introduced from the rectifier, or from elsewhere in the process, it can be introduced into the reboiler.

Monomer product (52) is recovered from the reboiler, or if one or more further reactors are used, from the last of them. If desired, this product can be fed directly to conventional polymerization equipment to form polyester. This equipment could include a prepolymer reactor and an esterification reactor. Alternatively, monomer can be collected, and stored prior to its being used, alone or in combination with other monomer, to prepare polyester.

The following example illustrates the practice of this invention.

EXAMPLE

The following example used apparatus schematically represented in FIG. 1. Scrap extruded polyethylene terephthalate sheet containing a blue dye and a polyvinylidene chloride coating was converted to bis(hydroxyethyl) terephthalate monomer using a continuous process of the present invention. Over a period of 3 hours 4 kg. of the scrap polyester was fed to the dissolver at the rate of 20 g. per minute. Melt is transferred from the dissolver to the reactor at 200 g. per minute and melt is recirculated at the same rate. The reactor was run at 275° C. and atmospheric pressure. Methanol was fed to the reactor at 80 grams/min. at 275° C. The rectifier on top of the reactor has approximately three ideal stages of packing and is operated at atmospheric pressure and 165° C. vapor temperature to create reflux. At this temperature, the overhead product is dimethyl terephthalate and ethylene glycol plus excess methanol. At this temperature the half ester, methylhydroxyethyl terephthalate, is in the liquid state and returns to the reactor for further reaction with methanol. At this temperature the blue dye (Miles Ceres XR-RF) contained in the scrap returns to the reactor.

When operating at steady state, the output of the rectifier provides a feed stream for the reactive distillation column that has a composition of 74 g/min. methanol, 17 g/min. dimethyl terephthalate and 5.5 g/min. ethylene glycol and minor low boiling impurities. Overhead products from the rectifier are fed to the center of the column. Approximately three ideal stages of packing are above the point of vapor introduction and two are below.

The reactive distillation column has a reboiler at the column base with a residence time of two hours. The reboiler is operated at atmospheric pressure and the boiling point of ethylene glycol, 196° C. Ethylene glycol is introduced from the reboiler to the base of the column at a rate of 50 g/min. In addition, 20 g/min ethylene glycol with 20 ppm zinc acetate catalyst is added as a liquid at the top of the column. This liquid contacts the vaporized dimethyl terephthalate and promotes monomer formation.

The temperature of the condenser at the top of the column is regulated to allow all of the methanol and the desired fraction of ethylene glycol to go overhead to the condenser. At 100° C., 18 percent of the ethylene glycol in the column goes out with overhead products. At 110° C., 27 percent of the ethylene glycol in the column goes out with overhead products, and at 120° C., 37 percent of the ethylene glycol in the column goes. Thus, the top temperature can be used to regulate the ethylene glycol balance and the rate of impurity removal. When the distillation column is operated in this way pure bis(hydroxyethyl) terephthalate monomer, plus excess ethylene glycol, is collected in the reboiler at the column base.

The monomer collected from the reboiler was stripped of excess ethylene glycol. This monomer was run in a standard polymerization reactor to produce polyethylene terephthalate having an intrinsic viscosity of 0.65. The transmission density of this polymer was measured and compared with that of the starting scrap and polyethylene terephthalate prepared from virgin monomer. The transmission density of a 7 mm thick sheet at 550 nm and 400 nm was measured. The values for each polymer at the two points was averaged to give an "absorbance color value," which is a measure of the yellowishness of the polyester. This is of significance because yellow is the color of deteriorated polyester. The results, shown in Table 1 below, confirm that the polymer is of a color acceptable for normal industrial applications.

TABLE 1

| Polyester | Absorbance Color Value |
|---|---|
| Starting scrap | 0.14 |
| From monomer recovered according to invention | 0.07 |
| From virgin monomer | 0.06 |

The invention has been described by reference to preferred embodiments, but it will be understood changes can be made to the apparatus and process steps specifically described herein within the spirit and scope of the invention.

What is claimed is:

1. A process for converting scrap polyester directly to monomer that can be used to reform the polyester using apparatus that comprises:
   a dissolver for receiving polyester,
   a reactor for depolymerizing polyester into monomer components,
   a rectifier for separating monomer components from high boiling impurities,
   a reactive distillation column for separating monomer components from low boiling impurities and for transesterifying dimethyl terephthalate and ethylene glycol to bis(hydroxyethyl)terephthalate and a reboiler from which heated ethylene glycol is introduced to the reactive distillation column;

the process comprising the steps of:
a) adding polyester to the dissolver and combining it with melt from the reactor to reduce polyester chain length,
b) transferring reduced chain length polyester from the dissolver to the reactor,
c) passing super-heated methanol through the reactor to depolymerize polyester,
d) transferring depolymerization products from the reactor to the rectifier;
e) separating the depolymerization products in the rectifier into a vapor phase, containing methanol and monomer components, and a liquid phase, containing higher molecular weight materials;
f) transferring the vapor phase to the reactive distillation column;
g) introducing ethylene glycol and an esterification catalyst into the distillation column
  i) to initiate a transesterification reaction between dimethyl terephthalate and ethylene glycol, and
  ii) to remove lower boiling components; and
h) continuing the transesterification reaction to form bis(hydroxyethyl) terephthalate.

2. A process of claim 1, wherein the transesterification reaction is completed in the reboiler.

3. A process of claim 1 wherein the transestrification process is completed in one or more additional transesterification reactors.

4. A process of claim 1, wherein the bis(hydroxyethyl) terephthalate is capable of yielding a polyester having an absorbance color value of less than 0.10.

5. A process of claim 1, wherein a condenser is attached to the top of the reactive distillation column and the temperature maintained in the condenser is used to control the ethylene glycol balance in the column.

6. A process of claim 5 wherein the condenser is operated at a temperature of about 100° to 120° C.

7. A process of claim 1, wherein the dissolver and reactive distillation column are operated at about atmospheric pressure and the reactor is operated at a pressure up to about 800 kPaa.

* * * * *